(12) United States Patent
Yoo

(10) Patent No.: US 7,635,585 B2
(45) Date of Patent: Dec. 22, 2009

(54) MICRO VALVE APPARATUS USING MICRO BEAD AND METHOD FOR CONTROLLING THE SAME

(75) Inventor: Jae Chern Yoo, 4-1505, Daehakwon Apt. 756 Jigok-dong, Nam-gu, Pohang-city, Kyungsangbuk-do (KR)

(73) Assignee: Jae Chern Yoo, Pohang (KR)

(*) Notice: Subject to any disclaimer, the term of this patent is extended or adjusted under 35 U.S.C. 154(b) by 220 days.

(21) Appl. No.: 10/479,004

(22) PCT Filed: May 31, 2002

(86) PCT No.: PCT/KR02/01035

§ 371 (c)(1),
(2), (4) Date: Nov. 25, 2003

(87) PCT Pub. No.: WO02/097422

PCT Pub. Date: Dec. 5, 2002

(65) Prior Publication Data

US 2004/0155213 A1    Aug. 12, 2004

(30) Foreign Application Priority Data

May 31, 2001 (KR) ............................... 2001-31284

(51) Int. Cl.
*C12M 1/00* (2006.01)
*C12Q 1/68* (2006.01)
*C12P 19/34* (2006.01)

(52) U.S. Cl. .................... 435/283.1; 425/6; 425/91.2

(58) Field of Classification Search ................... None
See application file for complete search history.

(56) References Cited

U.S. PATENT DOCUMENTS 1,994,924 A * 3/1935 Schaelchlin ................. 335/104

(Continued)

FOREIGN PATENT DOCUMENTS

DE      224384 A1 * 7/1985

(Continued)

OTHER PUBLICATIONS

Krusemark et al. Micro ball valve for fluidic micropumps and gases. Proc. Micro Total Analysis Systems '98 Workshop, pp. 399-402.*

*Primary Examiner*—Young J Kim
*Assistant Examiner*—Samuel Woolwine
(74) *Attorney, Agent, or Firm*—Staas & Halsey LLP

(57) ABSTRACT

A micro (thin film type) valve apparatus for controlling fluid flow and its rate using a microbead and a method for controlling the apparatus are provided. The microbead is moved by the magnetic forge generated by upper and lower electromagnets disposed on the top and bottom surface of the body or by the electric field generated by upper and lower electrode plates disposed on the top and bottom surface of the body, thereby interconnecting or blocking flow channels in the body. The micro valve apparatus and the method for controlling the same are suitable for thin film type diagnostic assay devices, such as lab-on-chips, protein chips, or DNA chips, for detecting small quantities of analytes in fluids, and more suitable for interconnecting or blocking channels formed in thin disk type apparatus including general CD-ROMs, DVDs, bioCDs, and bio DVDs.

19 Claims, 14 Drawing Sheets

U.S. PATENT DOCUMENTS

| | | |
|---|---|---|
| 3,335,946 A | 8/1967 | Putterlik |
| 3,899,296 A * | 8/1975 | Mailen et al. .................. 422/50 |
| 4,431,094 A * | 2/1984 | Parthuisot et al. ............ 192/3.3 |
| 4,581,624 A | 4/1986 | O'Connor |
| 4,938,742 A | 7/1990 | Smits |
| 5,711,347 A * | 1/1998 | Sturman et al. ......... 137/625.65 |
| 5,863,708 A * | 1/1999 | Zanzucchi et al. ........... 430/320 |
| 5,967,187 A * | 10/1999 | Horne et al. ................. 137/875 |
| 6,025,601 A | 2/2000 | Trulson et al. |
| 6,111,096 A | 8/2000 | Laugharn, Jr. et al. |
| 6,143,248 A | 11/2000 | Kellogg et al. |
| 6,157,043 A * | 12/2000 | Miyamoto ................... 257/22 |
| 6,167,910 B1 * | 1/2001 | Chow .......................... 137/827 |
| 6,319,469 B1 | 11/2001 | Mian et al. |
| 2001/0055812 A1 * | 12/2001 | Mian et al. .................... 436/45 |

FOREIGN PATENT DOCUMENTS

| | | | |
|---|---|---|---|
| GB | 1075800 | | 7/1967 |
| WO | WO 98/38510 | | 9/1998 |
| WO | WO 9853234 A1 | * | 11/1998 |
| WO | WO 99/64846 | | 12/1999 |
| WO | WO 00/17624 | * | 3/2000 |
| WO | WO 00/22436 | | 4/2000 |
| WO | PCT/KR02/01035 | * | 9/2003 |

* cited by examiner

MICRO VALVE APPARATUS USING MICRO BEAD AND METHOD FOR CONTROLLING THE SAME

This application is a 371 of PCT/KR02/01035 filed on May 31, 2002, published on Dec. 5, 2002 under publication number WO 02/097422 A1 which claims priority benefits from Korean patent application number KR 2001/31284 filed May 31, 2001.

TECHNICAL FIELD

The present invention relates to the field of controlling fluid flow and its rate in a micro assay device for the detection of a small quantity of an analyte in a fluid. More particularly, the present invention relates to a micro (thin film type) valve apparatus using a microbead to control fluid flow or its rate, and a method for controlling the micro valve apparatus.

BACKGROUND ART

To date, for most diagnostic assay apparatuses for the detection of small quantities of analytes in fluids, multiple-sample preparation and automated reagent addition devices, or multiple-sample assay apparatuses for identifying a number of samples at the same time, either in parallel or serial procession, have been designed to improve efficiency and economy. Such an automated reagent preparation device and an automated multiple-sample assay apparatus are integrated into a single thin film type apparatus. This thin film type diagnostic assay apparatus can automatically or semi-automatically accurately analyze hundreds of analytes using trace amounts of a sample and reagents. The thin film type assay apparatus needs a valve for automatically supplying a sample or reagents (enzyme and buffer). However, designing such a valve for a thin film type assay apparatus is complicated. Therefore, there is a need to design a simple valve suitable for the thin film type assay apparatus.

<Thin Film Type CD & DVD>

The standard compact disk is formed from a 12-cm polycarbonate substrate, a reflective metal layer, and a protective lacquer coating. DVD stands for digital video disk, a type of optical disk of the same size as the compact disk, but with significantly greater recording capacity.

The polycarbonate substrate is optical-quality clear polycarbonate. In a standard pressed CD or DVD, the data layer is part of the polycarbonate substrate, and the data are impressed as a series of pits by a stamper during injection molding. In the injection molding process, melted polycarbonate is injected into a mold under high pressure and cooled in a mirror image of the mold or stamper. As a result, reverse pits of the stamper are formed on the polycarbonate disk surface during mastering as binary data. The stamping master is typically glass.

Those disks can be modified into CD-ROMs, DVDs, bio-CDs or bio-DVDs as thin disk type diagnostic assay apparatuses for detecting non-biological analytes or biological molecules in a fluid. In this case, during injection molding, instead of the pits, channels as fluid flow paths and chambers as buffer reservoirs can be formed in the disk surface. Additionally, a thin film type valve for controlling fluid flow and its rate through the channels formed in the thin disk surface is required.

GB 1075800 (published Jul. 12, 1967), entitled "Disc for Centrifuge", disclosures a device for flowing a sample fluid supplied via an inject hole of the disc over the surface of the disc by centrifugal force. EP 3335946 (published Apr. 12, 1965), entitled "Separating Disks for Centrifuge", discloses an apparatus for separating fluid samples injected via an inject hole of the disc by flowing the samples through channels or chambers formed in the disc. However, these apparatuses failed to overcome the problems of the thin film type valve and to precisely control flow rate.

A general valve using an electromagnet opens or closes a flow path using a cylinder or a plunger that is moved by magnetic force. To intensify the magnetic force so as to move the cylinder or flange, a ferroelectric core of an appropriate size and a number of wires wound around the core are required. Also, a large amount of electricity is required to turn on or off the valve and move the cylinder or flange. The valve using the electromagnet cannot be constructed as a thin film type valve due to the size of the electromagnet. The valve generates excess heat by consuming a large amount of electricity. To address these problems, according to the present invention, electromagnets and a microbead are used. A valve using the microbead according to the present invention can be constructed in thin film form, and a small force is required to move the microbead. Accordingly, the electromagnets can be formed as thin films. Also, since electricity consumption is very low, no heat is generated when the valve is operated.

Therefore, the micro (thin film type) valve apparatus and the method for controlling the same according to the present invention are suitable for a thin film type diagnostic assay apparatus, such as a lab-on-a-chip, or DNA-chip, for detecting a small quantity of an analyte in a fluid, and especially, for interconnecting and blocking channels formed in a thin disk type assay device, such as a CD-ROM, a DVD, a bio-CD, and a bio-DVD, or for controlling the rate of fluid flowing.

Accordingly, it is an object of the present invention is to provide a micro (thin film type) valve apparatus and a method for controlling the same, in which a microbead that is moved by the magnetic or electric force generated by electromagnets or electrode plates installed on the top and bottom surfaces of its body is placed in the middle of channels to block or interconnect the channels.

It is another object of the present invention to provide a thin film type diagnostic assay apparatus for detecting a small quantity of an analyte using the micro (thin film type) valve apparatus for controlling fluid flow and its rate, and particularly, to provide an nucleic acid assay apparatus and method for detecting whether a sample contains a target nucleic acid or not, using the micro (thin film type) valve apparatus.

DISCLOSURE OF THE INVENTION

In one aspect, the present invention provides a micro valve apparatus comprising: channels as flow paths of a fluid; a hole which interconnects the channels; a thin disk type body in which the channels and the hole are formed; upper and lower electromagnets mounted on the top and bottom surfaces of the body, respectively, opposite to each other, which generate a magnetic force with the application of power; and a microbead which is moved upward or downward by on/off control of the power applied to the upper and lower electromagnets, to open and close the hole, thereby controlling fluid flow and its rate.

Alternatively, the present invention provides a micro valve apparatus comprising: channels as flow paths of a fluid; a hole which interconnects the channels; a thin disk type body in which the channels and the hole are formed; upper and lower electrode plates mounted on the top and bottom surfaces of the body, respectively, opposite to each other, which generate an electric field with the application of power; and a charged microbead which is moved upward or downward by controlling the direction in which power is applied to the upper and lower electrode plates, to open and close the hole, thereby controlling fluid flow and its rate.

In each of the micro valve apparatuses described above, the body may comprise a ventilating hole through which air is exhausted to allow smooth flow of the fluid. In this case, the ventilating hole is formed in an opposite direction to the direction in which the fluid flows or a centrifugal force is exerted.

In each of the micro valve apparatuses described above, the body may be formed of a material selected from the group consisting of plastic, polymethylmethacrylate (PMMA), glass, mica, and silica. Preferably, the microbead is formed of a material selected from the group consisting of ferroelectric particles, paramagnetic particles, diamagnetic particles, metal particles, metal-coated plastic particles, and metal-coated glass particles. Preferably, the microbead is spherical or non-spherical, and more preferably, spherical. Preferably, the non-spherical microbead is a thin cylindrical element or a thin rectangular element.

Preferably, the microbead has a diameter of 1 μm-1 mm, and more preferably, 100-500 μm. Preferably, the hole is rounded corresponding to a curvature of the microbead. Preferably, the hole includes an auxiliary inner hole having a diameter smaller than the microbead and/or an auxiliary outer hole having a diameter greater than the microbead.

In each of the micro valve apparatuses described above, the body may be a thin disk type apparatus selected from the group consisting of CD-ROM, DVD, bio-CD, and bio-DVD. Preferably, the body comprises a confining groove and/or a confining channel which holds the microbead and prevents it from leaving away.

Preferably, the body is constructed by binding upper, intermediate, and lower substrates together. In this case, two chambers and the hole are formed through the intermediate substrate, one chamber and an upper channel connecting the chamber and the hole are formed recessed to a depth in the upper substrate, and the other chamber and a lower channel connecting the chamber and the hole are formed recessed to a depth in the lower substrate.

In another aspect, the present invention provides a method for controlling the micro valve apparatus described above, which includes the upper and lower electromagnets, the method comprising: in order to block the channels by closing the hole of the micro valve apparatus, cutting off the power applied to the upper electromagnet and applying power to the lower electromagnet to attract the microbead to the hole; and in order to interconnect the channels with each other by opening the hole, cutting off the power applied to the lower electromagnet and applying power to the upper electromagnet to attract the microbead so as to be removed from the hole.

Alternatively, the present invention provides a method for controlling the micro valve apparatus described above, which includes the upper and lower electrode plates, the method comprising: in order to block the channels by closing the hole of the micro valve apparatus, applying a voltage of the same polarity as the charge of the microbead to the upper electrode plate to repel the charged microbead and applying a voltage of the opposite polarity to the lower electrode plate to attract the charged microbead to the hole; and in order to interconnect the channels with each other by opening the hole, applying a voltage of the same polarity as the charge of the microbead to the lower electrode plate to repel the charged microbead and applying a voltage of the opposite polarity to the upper electrode plate to attract the charged microbead so as to be removed from the hole.

In another aspect, the present invention provides a nucleic acid assay device in which fluid flow between chambers is controlled by one of the micro valve apparatuses described above, the device comprising: a sample injection unit via which a nucleic acid containing sample is injected; a preparation chamber where DNAs or RNAs are prepared from the nucleic acid containing sample; a PCR (polymerase chain reaction) chamber where the DNAs or RNAs are amplified through PCR or RT-PCR; an array chamber where the amplified DNAs or cDNAs are hybridized to a capture probe; a trash chamber where the non-hybridized waste from the array chamber is collected; and a plurality of chambers for storing a variety of enzymes and buffer solutions required for processes.

Preferably, the nucleic acid assay device is a lab-on-a-chip where the preparation chamber, the PCR chamber, the trash chamber, channels, and holes are formed in a disk type body. In this case, the disk type body may be constructed by binding the upper, intermediate, and lower substrates together.

In the nucleic acid assay device according to the present invention, it is preferable that opening or closing of the holes of the micro valve apparatus at the start and end of each of the processes is controlled by on/off control of the power applied to the upper and lower electromagnets or by controlling the direction in which power is applied to the upper and lower electrode plates, and that the fluid flow is induced by the centrifugal force which occurs as the disk type body is rotated.

In anther aspect, the present invention provides a nucleic acid assay method in the nucleic acid assay device described above, the method comprising: (a) injecting a nucleic acid containing sample into the preparation chamber via the sample injection unit; (b) preparing DNAs or RNAs from the nucleic acid containing sample; (c) opening a first hole between the preparation chamber and the PCR chamber and rotating the nucleic acid assay device for a predetermined period of time, to transfer the prepared DNAs or RNAs to the PCR chamber; (d) closing the first hole, opening a second hole between a chamber which store enzymes and buffer solutions required for PCR and the PCR chamber, and performing the PCR or RT-PCR to amplify the DNAs or RNAs; (e) after the PCR or RT-PCR has completed, closing the second hole, opening a third hole between the PCR chamber and the array chamber, and rotating the nucleic acid assay device for a predetermined period of time, to transfer the amplified DNAs or dDNAs to the array chamber; (f) closing the third hole, opening a fourth hole between a chamber which stores enzymes and buffer solutions required for hybridization and the array chamber, and performing the hybridization; and (g) after the hybridization has completed, closing the fourth hole, opening a fifth hole between the array chamber and the trash chamber, and rotating the nucleic acid assay device for a predetermined period of time, to collect the waste from the hybridization within the trash chamber.

The present invention will be described in greater detail with reference to the appended drawings.

Referring to FIGS. 1A and 1B, a body 100 or solid substrates 1, 2, and 3 can be formed of a variety of materials, including plastic, polymethylmethacrylate (PMMA), glass, mica, silica, etc. However, among those materials, plastic is most preferred for economical reasons, convenience of processing, and compatibility with existing laser reflection-based detectors for CD-ROMs and DVDs. Suitable plastics include polypropylenes, polyacrylates, polyvinyl alcohols, polyethylenes, polymethylmethacrylates, and polycarbonates. Among those materials, polypropylenes and polycarbonates are more preferred, with polycarbonates being most preferred.

In an embodiment according to the present invention, the microbead includes, for examples, ferroelectric particles, paramagnetic particles, diamagnetic particles, metal particles, etc. The microbead can be formed of plastic or glass particles, which is further coated with a metal. Alternatively, the metal particles for the metal bead can be metal-alloy particles. The microbead can be charged. In this case, instead of electromagnets, electrode plates are arranged on the top and bottom surfaces of the body 100. The charged microbead can be moved according to the direction in which a voltage is applied to the electrode plates, to open or close a hole connecting channels.

The microbead has a diameter of 1 µm-1 mm, and preferably, 100 µm-500 µm. When the diameter of the microbead is increased, the hole can be opened or plugged with higher reliability due to an increase in the contact area between the hole and the microbead.

Microbeads suitable for use in the valve apparatus according to the present invention are readily available in varying diameters from Aldrich Chemical Company, British BioCell International, Nanoprobes, Inc. It will be appreciated by those skilled in the art that the diameter of the microbead can be increased or reduced as needed.

The micro (thin film type) valve apparatus according to the present invention includes a body 100 having an inlet 11a, an outlet 11b, channels 22, and a ventilating hole 12, electromagnets 4a and 4b mounted on the opposite surfaces of the body 100 to generate a magnetic force with the application of power, a hole 10 connecting the channels 22 in the body 100, and a microbead 70 that is moved upward or downward by the magnetic force generated by the electromagnets 4a and 4b to open or close the hole 10, thereby controlling fluid flow and its rate.

In the present invention, preferably, the electromagnets 4a and 4b are thin electromagnets with an air core. As described above, the microbead 70 can be a magnetic ball, a thin cylindrical magnet, or thin rectangular magnet (bar magnet). As power is applied to the electromagnets 4a or 4b, the spherical magnet, thin cylindrical magnet, or thin rectangular magnet is attracted to the electromagnets 4a or 4b.

FIGS. 1A and 1B are sectional views for illustrating the operation of the micro (thin film type) valve apparatus using the microbead according to the present invention. Reference numerals 1, 2, and 3 denote three substrates constituting the body 100.

The body 100 is constituted by the upper substrate 1, the intermediate substrate 2, and the lower substrate 3. While the upper substrate 1, the intermediate substrate 2, and the lower substrate 3 are formed by injection molding, the channels 22 as flow paths, chambers 20 and 22 as buffer reservoirs, and the hole 10 connecting the channels 22 are formed. The upper substrate 1, the intermediate substrate 2, and the lower substrate 3 are bound together to form a single body 100.

FIG. 1A illustrates the state where the hole 10 is plugged by the microbead 70 to block the channels 22, and FIG. 1B illustrates the sate where the microbead 70 is removed from the hole 10 to interconnect the channels 22 with each other. To block the channels 22 by plugging the hole 10 with the microbead 70, as shown in FIG. 1A, power is applied to the lower electromagnet 4b while the power applied to the upper electromagnet 4a disposed opposite to the lower electromagnet 4b is cut off. To interconnect the channels 22 by opening the hole 10, as shown in FIG. 1B, power is applied to the upper electromagnet 4a while the power applied to the lower electromagnet 1b is cut off.

According to the present invention, since the channels 22 formed in the thin film type body 100 are narrow, the ventilating hole 12 is formed in the upper substrate 1 to reduce the air pressure and allow a fluid to smoothly flow through the channels 22.

Also, a confining groove 101 is formed in the upper substrate 1 to receive the microbead 70 when the channels 22 are interconnected with each other, as shown in FIG. 1B. The confining groove 101 holds the microbead 70 and prevents the microbead 70 from dropping into and plugging the hole 10 when the body 100 shakes. Preferably, the curvature of the confining groove 101 is about 50-70% greater than that of the microbead 70.

FIGS. 2A, 2B, 2C, and 2D illustrate a variety of embodiments of the hole 10 in the micro valve apparatus using the microbead 70 according to the present invention. Reference numeral 10 denotes a contact region between the microbead 70 and the intermediate substrate 2. The contact region is rounded corresponding to the curvature of the microbead 70 to prevent a leakage of the fluid when the hole 10 is plugged by the microbead 70.

Reference numeral 10a denotes the outer margin (also referred to as "outer hole"), and reference numeral 10b denotes the inner margin (also referred to as "inner hole") of the contact region. When the contact region is larger, the leakage of the fluid can be more effectively prevented. Preferably, the contact region has a diameter of 100-500 µm.

FIG. 2B illustrates another embodiment of the hole 10 where the inner hole 10b has an auxiliary inner hole 19b. This structure with the auxiliary inner hole 19b is suitable when a thickness of the intermediate substrate 2 is greater than the radius of the microbead 70. FIG. 2C illustrates another embodiment of the hole 10 where the outer hole 10a and the inner hole 10b have respective auxiliary holes 19a and 19b. When the channels 22a and 22c are interconnected with each other, due to the auxiliary outer hole 19a, the distance by which the microbead 70 is moved above to open the hole 12 can be reduced.

FIG. 2B illustrates another embodiment of the hole 10 in the micro valve apparatus according to the present invention when a thin cylindrical element or a thin rectangular element is used as the microbead 70'. Reference numeral 10 denotes a contact region between the thin cylindrical or rectangular element 70' and the intermediate substrate 2. Reference numeral 10a denotes the outer margin ("outer hole") of the contact region, and reference numeral 10b denotes the inner margin ("inner hole") of the contact region. A confining groove 101' is formed in the upper substrate 1 to receive the thin cylindrical or rectangular element 70' when the channels 22a and 22c are interconnected with each other. The confining groove 101' holds the thin cylindrical or rectangular element 70' and prevents it from dropping into and plugging the hole 10 when the body 100 shakes.

FIGS. 3A, 3B, and 3C illustrate the upper substrate 1, the intermediate substrate 2, and the lower substrate 3, respectively, of the micro (thin film type) valve apparatus using the microbead according to the present invention, where the channels 22, the hole 10, and the chambers 20 and 21, which are described above, are formed. The upper substrate 1, the intermediate substrate 2, and the lower substrate 3 are bound together to form a single body 100. Although not illustrated in FIGS. 3A, 3B, and 3C, the inlet is formed on the left, and the outlet is formed on the right. In FIGS. 3A, 3B, and 3C, the filled-in elements (black) are formed through the substrate, and the other elements (white) are formed recessed to a depth in the substrate.

As the upper substrate 1, the intermediate substrate 2, and the lower substrate 3 are bound together, the elements 20a, 20b, 20c form the chamber 20 near the inlet, and the elements 21a, 21b, and 21c form the chamber 21 near the outlet. In FIG. 3A, reference numeral 22a denotes an upper channel connected to an outlet of the chamber 20a formed in the upper substrate 1. In FIG. 3C, reference numeral 22c denotes a lower channel connected to an inlet of the chamber 21c formed in the lower substrate 3. In FIG. 3B, reference numeral 10 denotes the hole whose wall is rounded to fit to the microbead 70.

At one end of the upper and lower channels 22a and 22c, respective upper and lower confining channels 23a and 23c are formed. The upper and lower confining channels 23a and 23c have a diameter that is a little greater than the microbead 70 to prevent the microbead 70 from leaving away when the body 100 shakes. As the upper substrate 1, the intermediate substrate 2, and the lower substrate 3 are bound together to form the body 100, the upper confining channel 23a, the hole 10, and the lower confining channel 23c are interconnected with one another to form a single hole unit. The hole is opened or plugged by the microbead 70 that is moved by the magnetic force generated by the upper and lower electromagnets 4a and 4b. To prevent the microbead 70 from leaving away, the upper and lower confining channels 23a and 23c have a diameter that is preferably 30-60% greater than the microbead 70.

FIGS. 3A and 3D are bottom and top views of the upper substrate 1, respectively. In the top view of FIG. 3D, the ventilating hole 12 is apparent. In the micro valve apparatus according to the present invention, a fluid flows by centrifugal force or external pressure. To prevent the fluid from entering the ventilation hole 12, a ventilating path 24 connected to the ventilating hole 12 is formed toward the inlet of the body 100, i.e., opposite to the direction in which the centrifugal force is exerted.

In another aspect of the present invention, there is provided a method for controlling fluid flow and its rate in the micro (thin film type) valve apparatus using the microbead, by controlling the duration of time in which the hole is opened or closed by the microbead that is moved by the magnetic force generated by the upper or lower electromagnets In the method for controlling the micro valve apparatus using the microbead according to the present invention, to block fluid flow through the channels 20 and 21 in the micro valve apparatus, the power applied to the upper electromagnet 4a is cut off, and power is applied to the lower magnet 4b to attract the microbead 70 to the hole 10, thereby plugging the hole 10. In contrast, to interconnect the channels 20 and 21 with each other to allow fluid flow, the power applied to the lower electromagnet 4b is cut off, and power is applied to the upper electromagnet 4a to pull the microbead 70 so as to be removed from the hole 10.

In another aspect of the present invention, there is provided a method for controlling fluid flow and its rate in a micro valve apparatus using a charged microbead, in which the charged microbead is moved using a charged microbead, in which the charged microbead is moved by an electric field generated by upper and lower electrode plates 4a' and 4b' of the body, to open or close the hole, thereby controlling fluid flow and its rate. In this embodiment, the upper and lower electromagnets 4a and 4b used in the previous embodiment are replaced by the upper and lower electrode plates 4a' and 4b'.

With the assumption that a positively charged microbead is used, the operation for controlling the micro valve apparatus to open or close the hole 10 will be described. To block fluid flow through the channels 20 and 21, a positive voltage is applied to the upper electrode plate 4a' to repel the positively charged microbead 70 and move it toward the hole 10, and a negative voltage is applied to the lower electrode plate 4b' to attract the positively charged microbead to the hole 10, thereby plugging the hole 10. In contrast, to interconnect the channels 20 and 21 with each other to allow fluid flow, a negative voltage is applied to the upper electrode plate 4a' to attract the positively charge microbead 70 so as to be removed from the hole 10, and a positive voltage is applied to the lower electrode plate 4b' opposite to the upper electrode plate 4a' to increase the rate of fluid flowing through the hole 10.

BEST MODE FOR CARRYING OUT THE INVENTION

The present invention will be described in greater detail with reference to the following embodiments. The following embodiments are for illustrative purposes and are not intended to limit the scope of the invention.

<Nucleic Acid Assay Device>

Figure 1A:
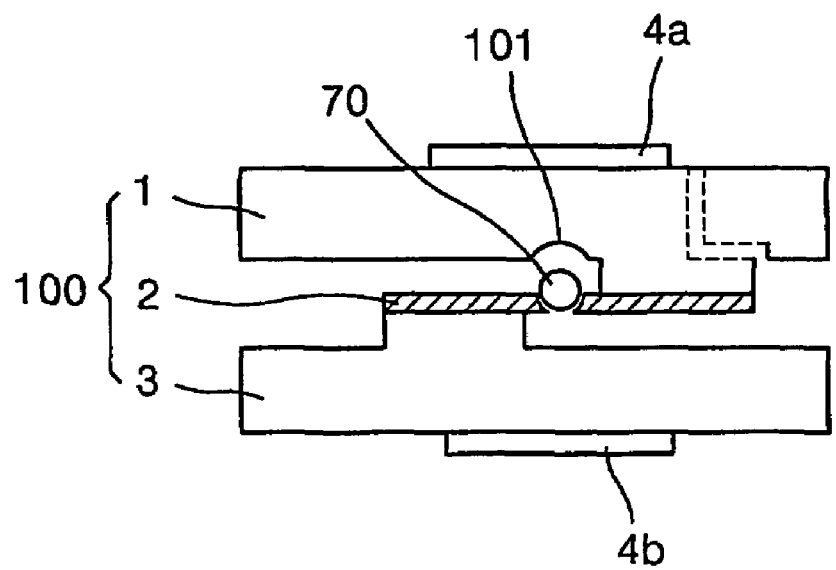
FIGS. 1A and 1B are sectional views for illustrating the states where a micro valve apparatus using a microbead according to the present invention operate.
Figure 1B:
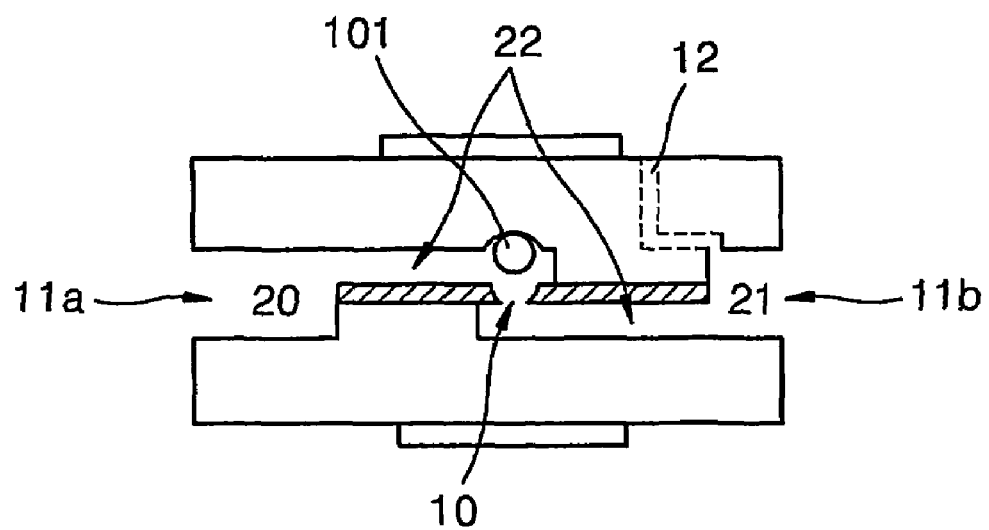
Figure 2A:
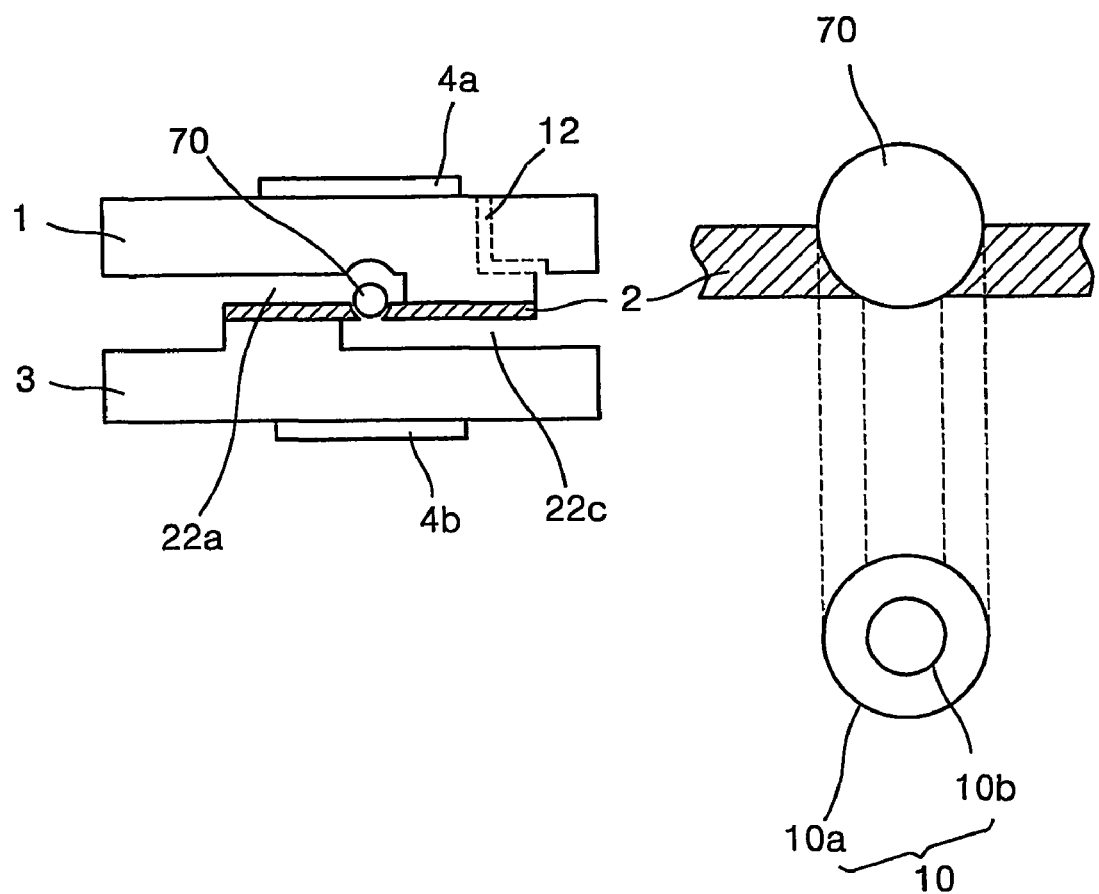
FIGS. 2A, 2B, 2C, and 2D illustrate a variety of embodiments of a hole in the micro valve apparatus using the microbead according to the present invention.
Figure 2B:
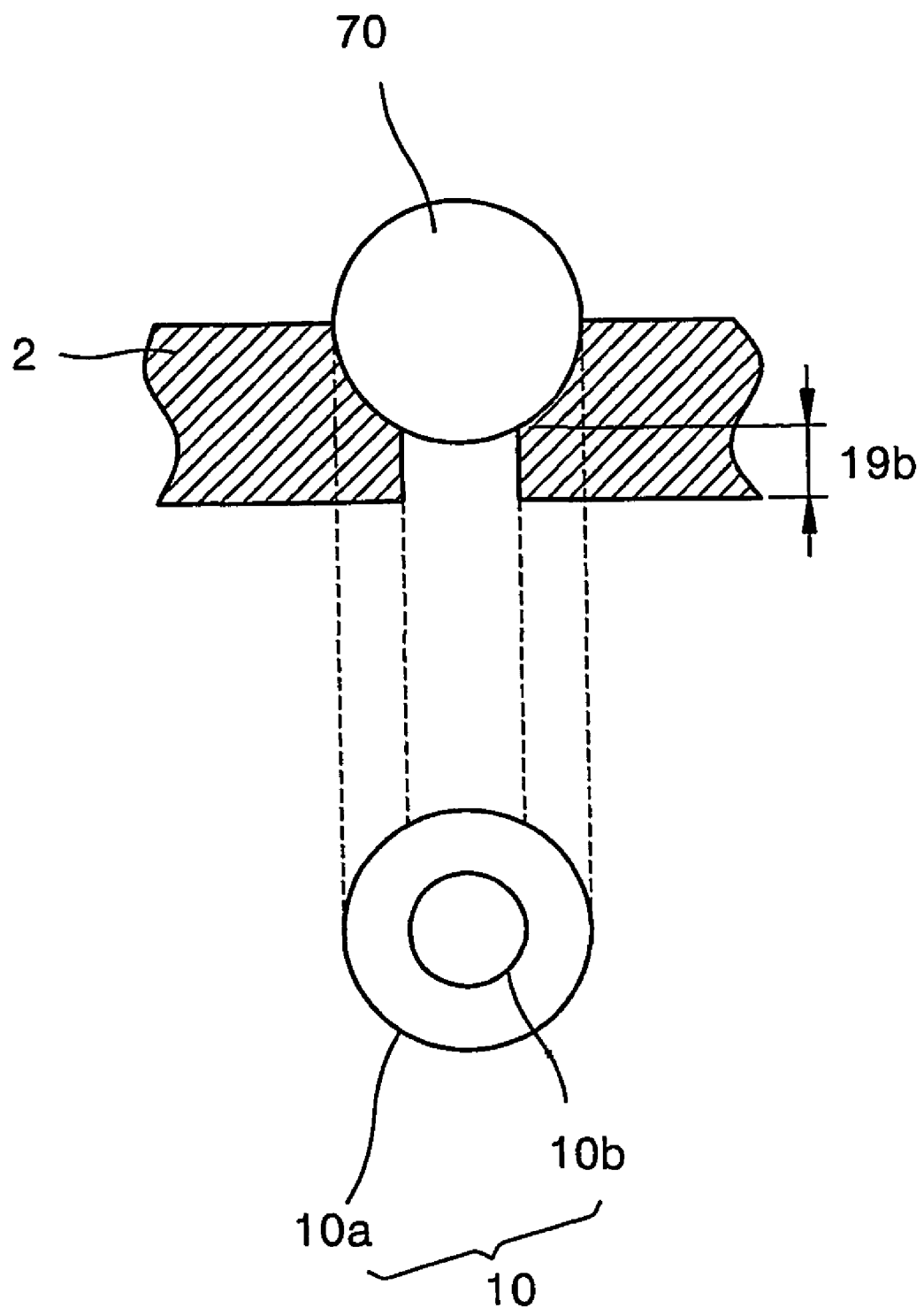
Figure 2C:
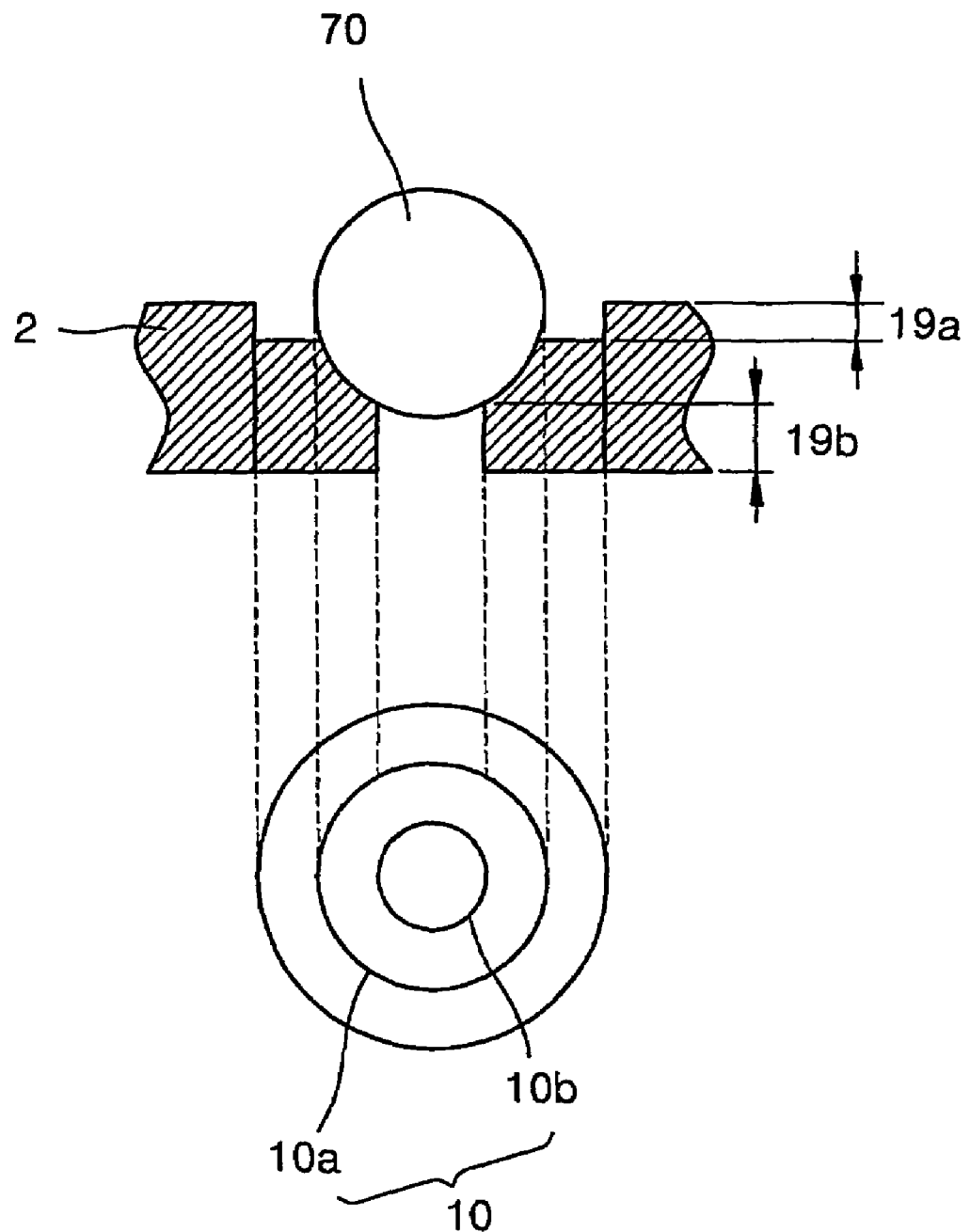
Figure 2D:
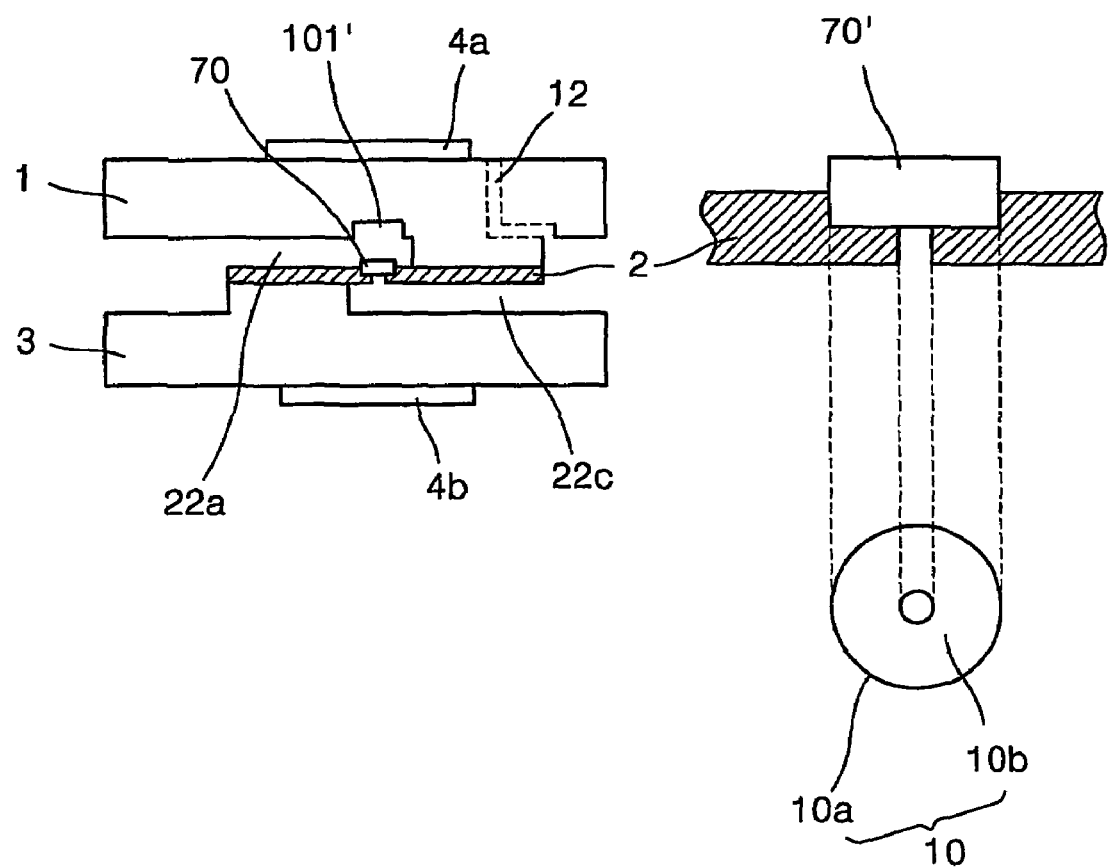
Figure 3A:
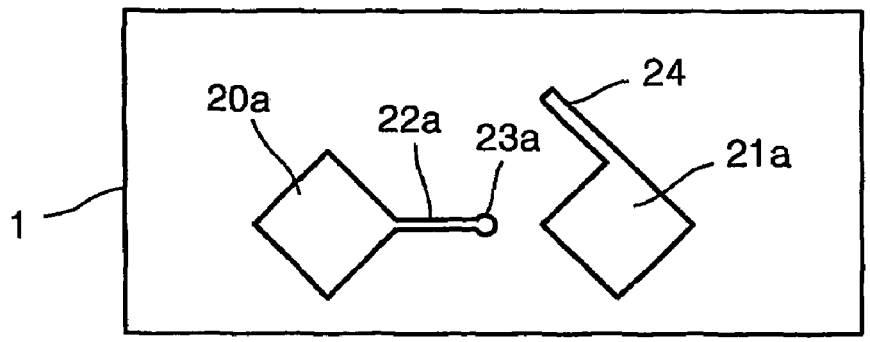
FIGS. 3A, 3B, 3C, and 3D illustrate upper, intermediate, and lower substrates of the micro valve apparatus using the microbead according to the present invention, where channels, a hole, chambers, a ventilating hole are formed.
Figure 3B:
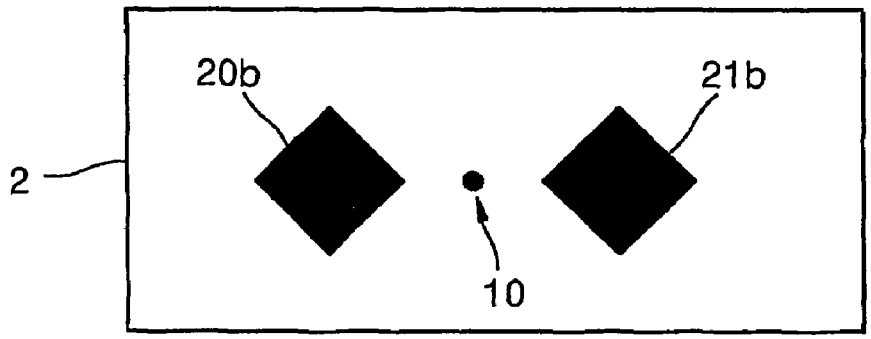
Figure 3C:
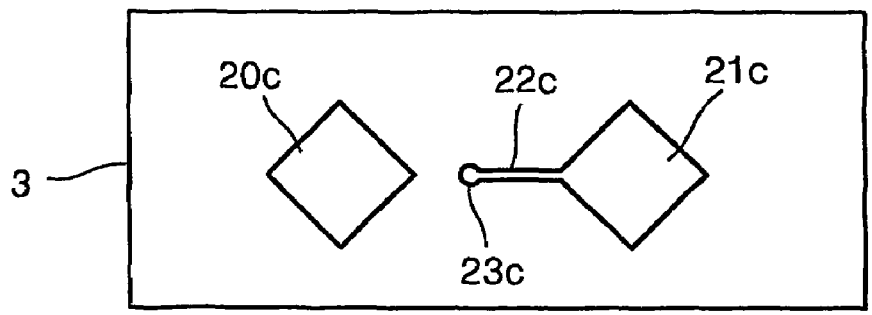
Figure 3D:
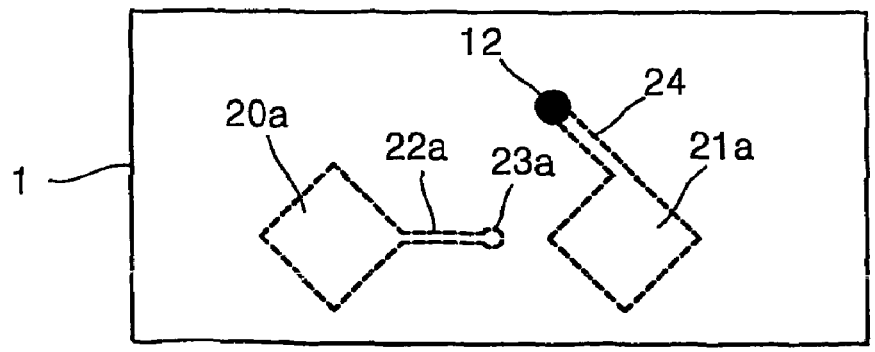
Figure 4:
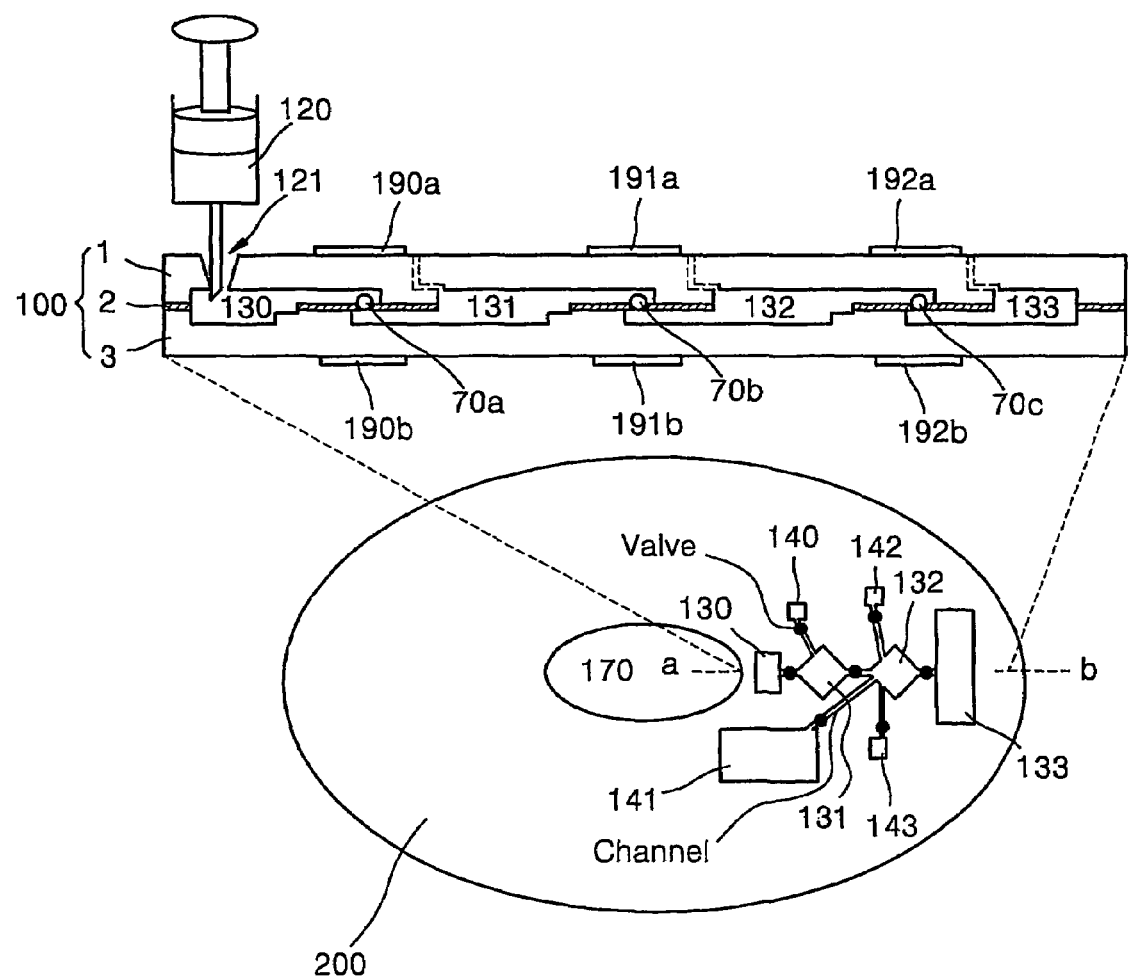
FIG. 4 shows an embodiment of the micro valve apparatus using the microbead according to the present invention applied to a thin disk type lab-on-a-chip, such as a general CD-ROM, DVD, bio-CD, or bio-DVD.

FIG. 4 shows a plan view and a sectional view, taken along line a-b, of an nucleic acid assay device constructed as a lab-on-a-chip according to an embodiment of the present invention, where the micro valve apparatus using a microbead according to the present invention is installed in a thin disk type apparatus 200. The thin disk type apparatus 200 may be a general CD-ROM, DVD, bio-CD, or bio-DVD.

Reference numeral 100 denotes a body constructed by binding the upper substrate 1, the intermediate substrate 2, and the lower substrate 3 together. Microbeads 70a, 70b, and 70c are independently moved by the magnetic force generated by electromagnetic pairs 190a 190b, 191a and 191b, and 192a and 192b, respectively, to open or close holes. Reference numeral 120 denotes a pipette or syringe for sample injection, reference numeral 121 denotes a sample inlet, and reference numeral 170 denotes a disk hole.

An example of the arrangement of chambers for storing a variety of assay buffers and for chemical reactions, channels along which sample fluids and the buffers flow, and valves for controlling the channels to be blocked or interconnected with each other, in the thin disk type apparatus is shown in FIG. 4.

In FIG. 4, reference numeral 130 denotes a preparation chamber where a DNA or RNA sample is prepared from blood or cells. Reference numeral 131 denotes a polymerase chain reaction (PCR) chamber where PCR or RT-PCR takes place, reference numeral 132 denotes an array chamber where the amplified DNA or cDNA fragments are hybridized to capture probes specific for a target DNA, which are immobilized on a substrate as an array. Reference numeral 133 denotes a trash chamber for collecting waste generated through a wash process. Reference numeral 140 denotes a chamber for storing a buffer solution including polymerases, used for the PCR in the PCR chamber 131. Reference numerals 141, 142, and 143 denote chambers for storing a variety of enzymes and buffers used for the hybridization in the array chamber 132.

Opening and closing of the valves (holes) at the start and end of each of the processes (preparation, PCR, hybridization, and washing process) is controlled by on/off control of the power applied to the electromagnet pair arranged above and below each of the microbeads. Fluid flow in the apparatus is induced by the centrifugal force which occurs as the disk type apparatus 200 is rotated.

Figure 5A:
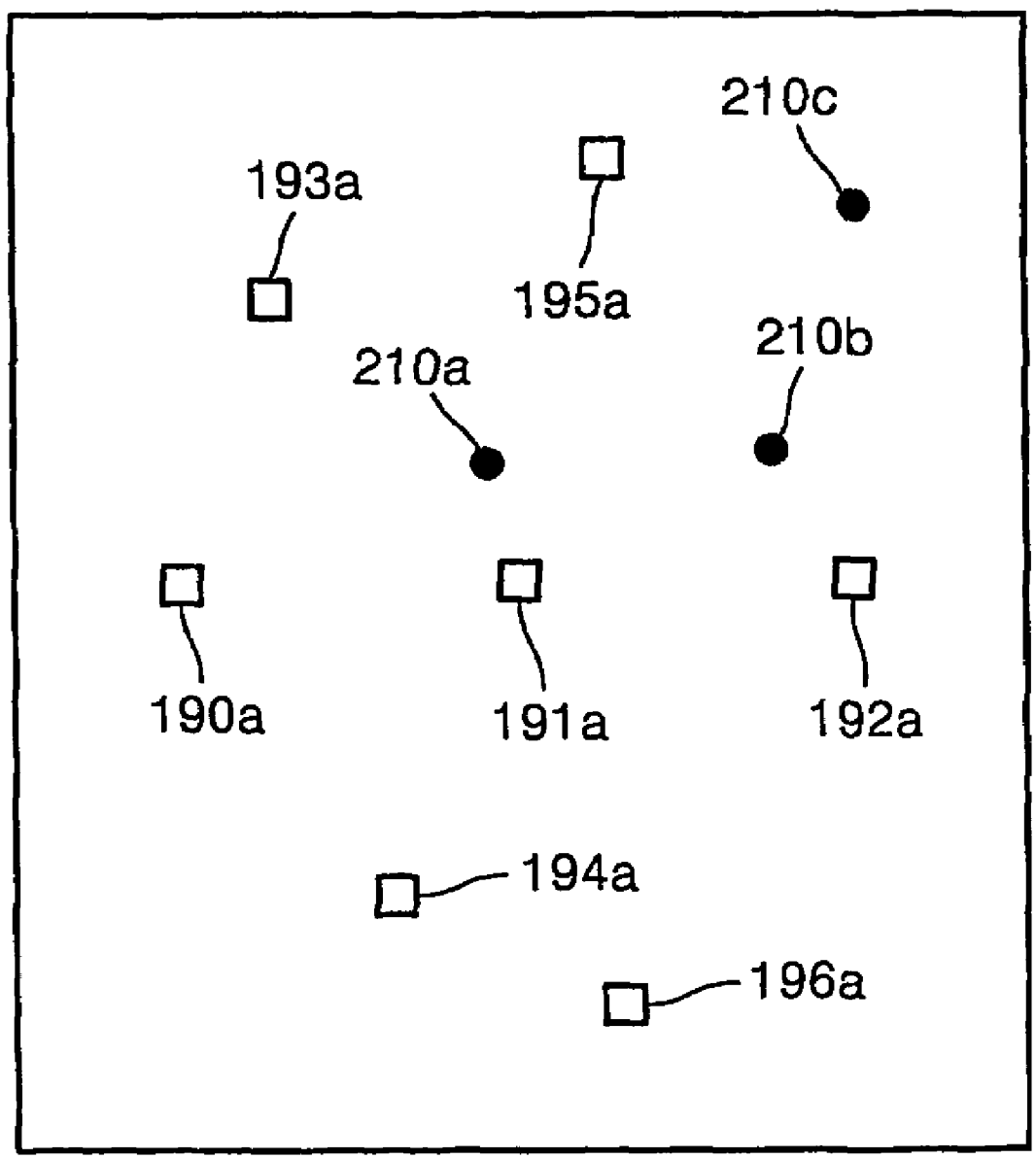
FIGS. 5A and 5B are top and bottom views of the upper substrate as a constituent of the body of the micro valve apparatus using the microbead according to the present invention, respectively, where channels, holes, chambers, and upper electromagnets are formed.
Figure 5B:
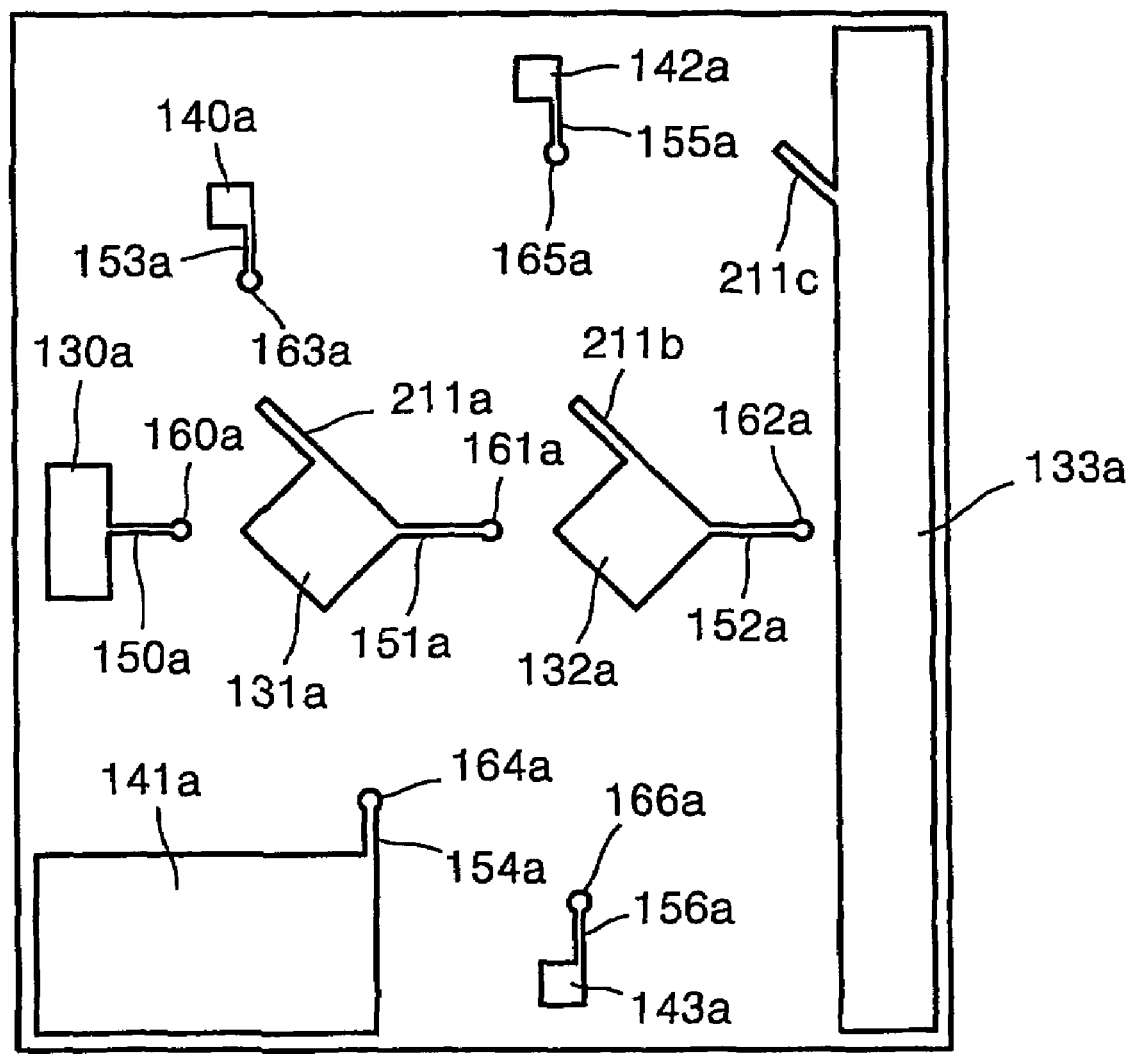
Figure 6A:
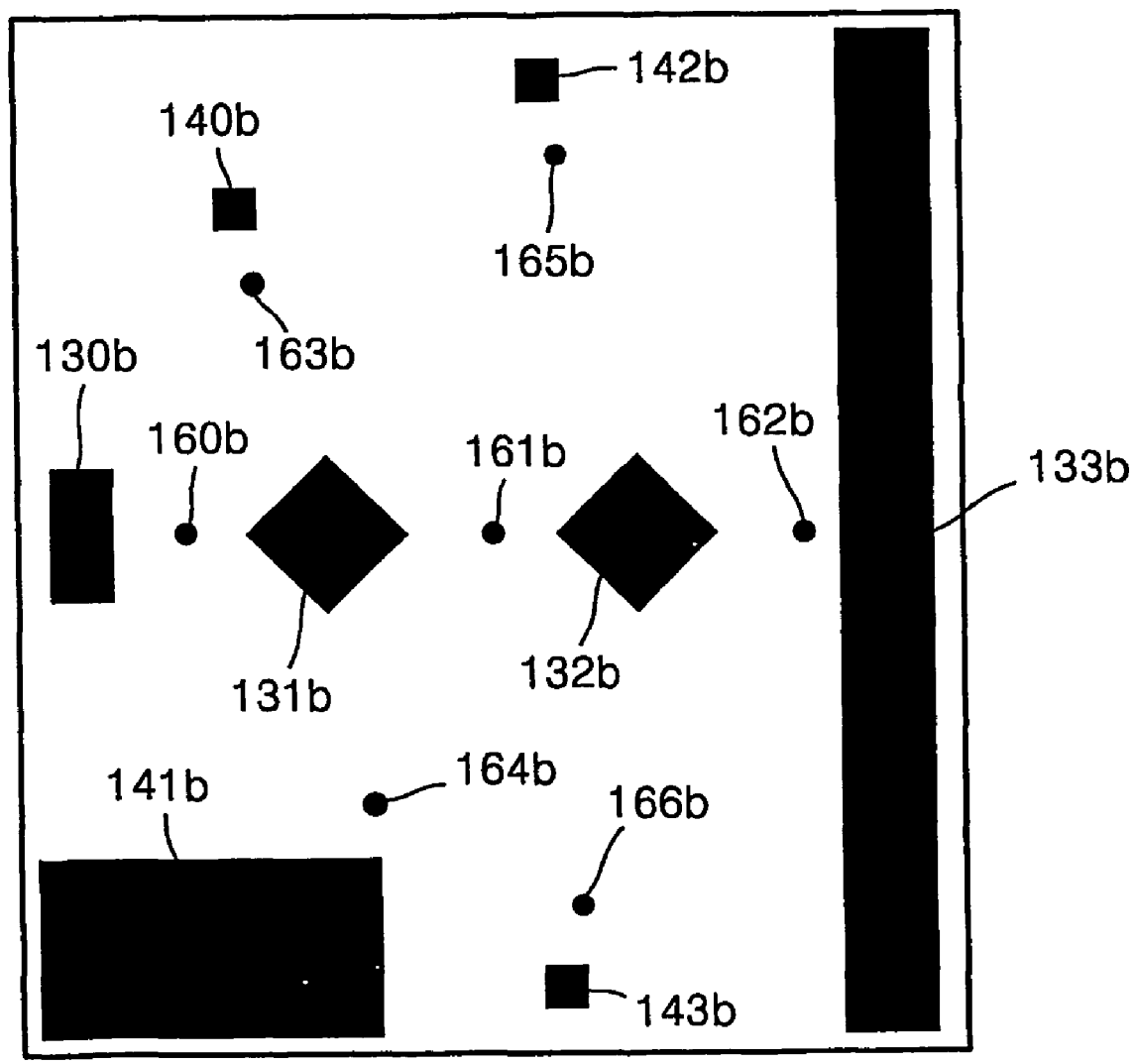
FIGS. 6A and 6B are top and bottom views of the intermediate substrate as a constituent of the body of the micro valve apparatus using the microbead according to the present invention, respectively, where holes and channels are formed.
Figure 6B:
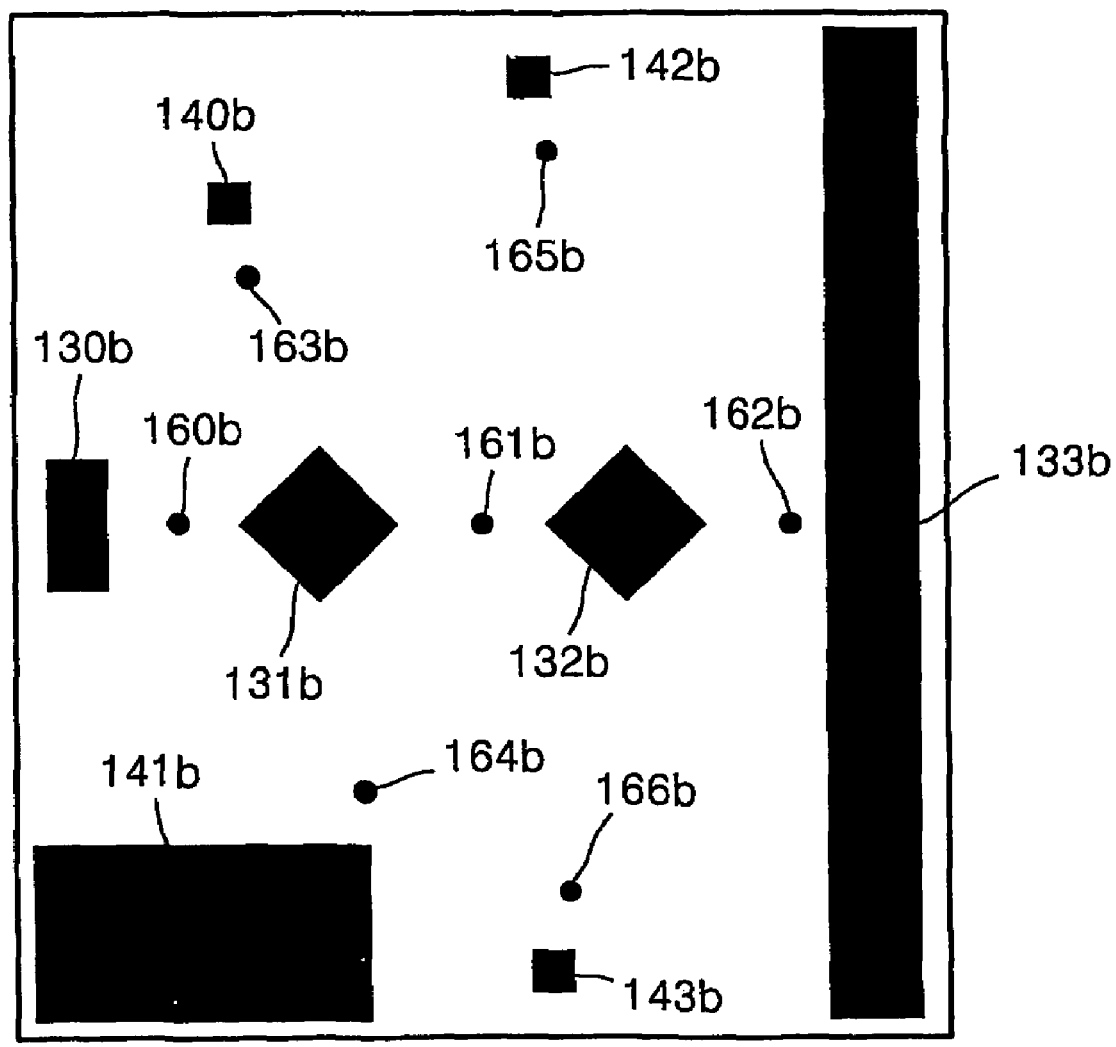
Figure 7A:
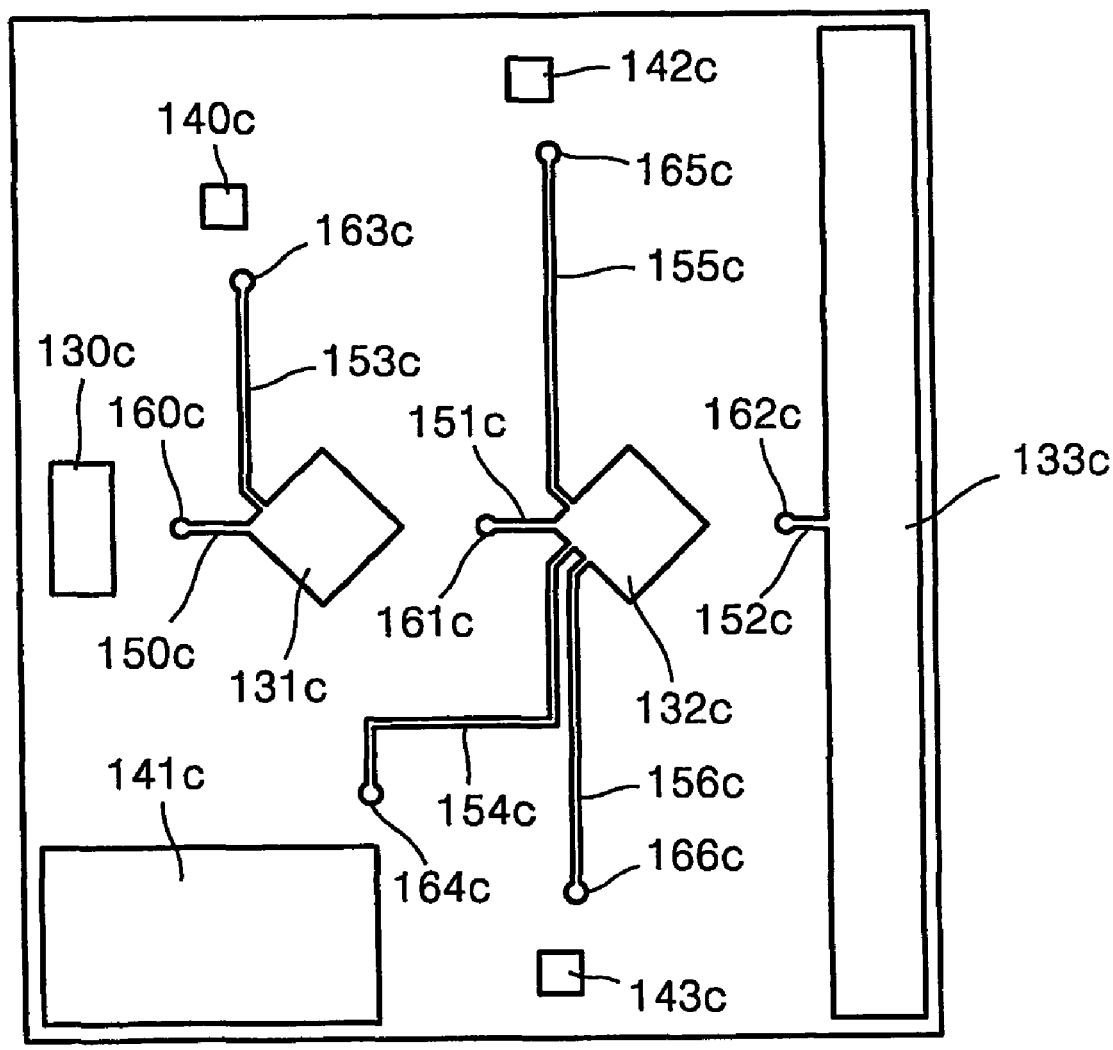
FIGS. 7A and 7B are top and bottom views of the lower substrate as a constituent of the body of the micro valve apparatus using the microbead according to the present invention, respectively, where channels, holes, chambers, and lower electromagnets are formed.
Figure 7B:
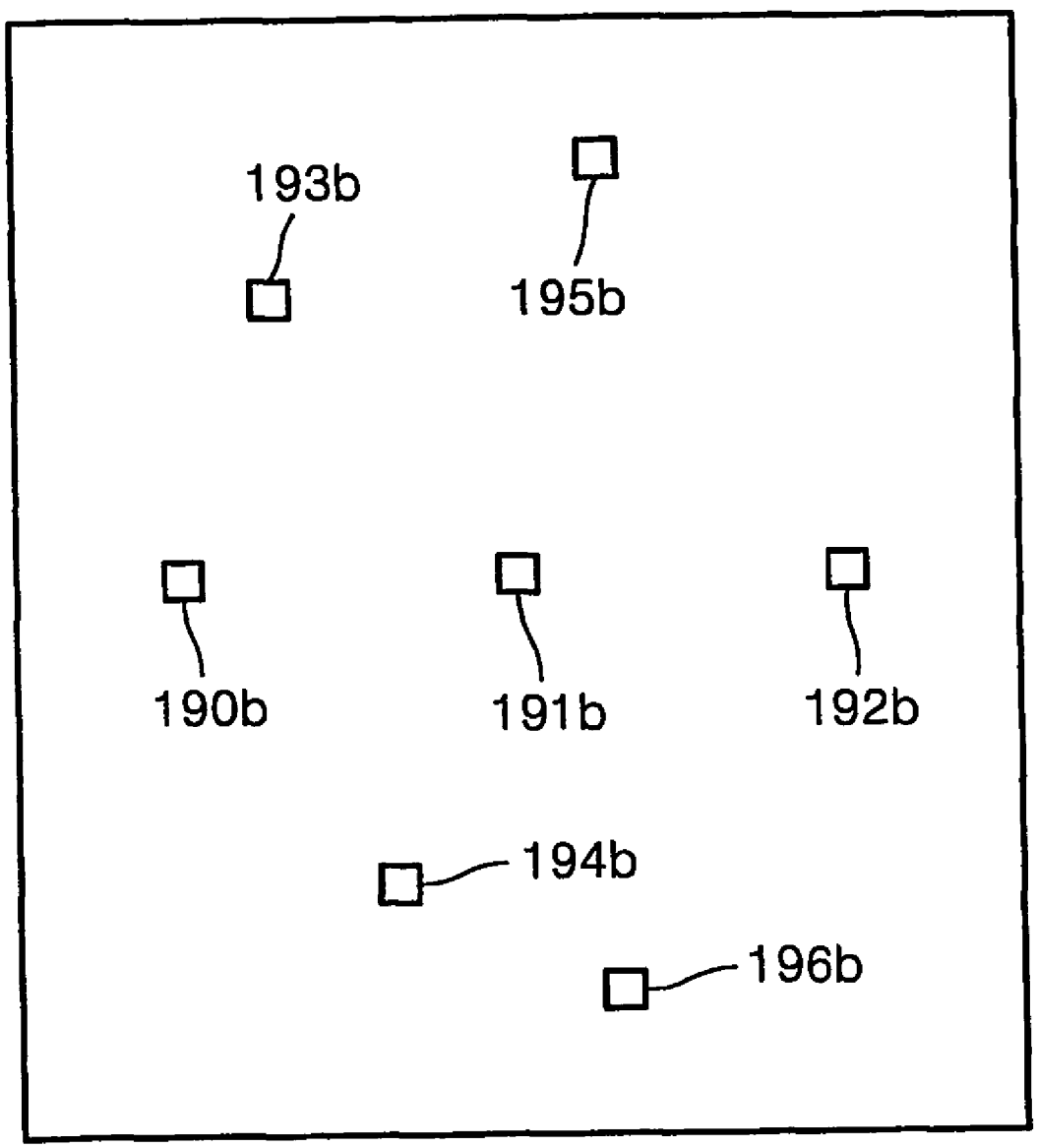

FIGS. 5A and 5B are top and bottom views of the upper substrate 1 as a constituent of the body 100 of the micro valve apparatus using the microbead according to the present invention, respectively, where channels, holes, chambers, and upper electromagnets are formed. FIGS. 6A and 6B are top and bottom views of the intermediate substrate 2 as a constituent of the body 100 of the micro valve apparatus using the microbead according to the present invention, respectively, where holes and channels are formed. FIGS. 7A and 7B are top and bottom views of the lower substrate 2 as a constituent of the body 100 of the micro valve apparatus using the microbead according to the present invention, respectively, where channels, holes, chambers, and lower electromagnets are formed. In FIGS. 5A, 5B, 6A, 6B, 7A, and 7B, the filled-in elements are formed through the corresponding substrate, and the other elements are formed recessed to a depth in the corresponding substrate. The upper substrate 1, the intermediate substrate 2, and the lower substrate 3 are bound together to form a single body 100.

As the upper substrate 1, the intermediate substrate 2, and the lower substrate 3 are bound together, the elements 130a, 130b, and 130c form the preparation chamber 130, the elements 131a, 131b, and 131c form the PCR chamber 131, the elements 132a, 132b, and 132c form the array chamber 132, and the elements 133a, 133b, and 133c form the trash chamber 133. The elements 140a, 140b, and 140c form the chamber 140 for storing a variety of enzymes and buffer use for PCR. The elements 141a, 141b, and 141c form the chamber 141, the elements 142a, 142b, and 142c form the chamber 142, and the elements 143a, 143b, and 143c form the chamber 143, which store a variety of enzymes and buffers used for hybridization.

In FIG. 5B, reference numeral 150a denotes an upper channel connected to an outlet of the preparation chamber 130a which is formed in the upper substrate 1301, reference numeral 151a denotes an upper channel connected to an outlet of the PCR chamber 131a which is formed in the upper substrate 1, and reference numeral 152a denotes an upper channel connected to an output let of the array chamber 132a which is formed in the upper substrate 1. Reference numeral 153a denotes an upper channel connected to an outlet of the chamber 140a which is formed in the upper substrate 1, reference numeral 154a denotes an upper channel connected to an outlet of the chamber 141 which is formed in the upper substrate 1, reference numeral 155a denotes an upper channel connected to an outlet of the chamber 142a which is formed in the upper substrate 1, and reference numeral 156a denotes an upper channel connected to an outlet of the chamber 143a which is formed in the upper substrate 1. Reference numerals 211a, 211b, and 211c denote ventilating paths connected to the PCR chamber 131, the array chamber 132, and the trash chamber 133, respectively.

In FIG. 5A, upper electromagnets 1901, 191a, 192a, 193a, 194a, 195a, and 196a mounted on the top of the upper substrate 1, and ventilating holes 210a, 210b, and 210c connected to the ventilating paths 211a, 211b, and 211c, respectively, are shown.

In FIG. 7A, reference numeral 150c denotes a lower channel connected to an inlet of the PCR chamber 131c which is formed in the lower substrate 3, reference numeral 151c denotes a lower channel connected to an inlet of the array chamber 132c which is formed in the lower substrate 3, reference numeral 152c denotes a lower channel connected to an inlet of the trash chamber 133c which is formed in the lower substrate 3, and reference numeral 153c denotes a lower channel connected to an inlet of the PCR chamber 131c which is formed in the lower substrate 3. Reference numerals 154c, 155c, and 156c denote lower channels connected to inlets of the array chamber 132c which is formed in the lower substrate 3, respectively.

At one end of the upper channels 150a, 151a, 152a, 153a, 154a, 155a, and 156a, upper confining channels 160a, 161a, 162a, 163a, 164a, 165a, and 166a each of which has a predetermined diameter are formed, respectively. At one end of the lower channels 150c, 151c, 152c, 153c, 154c, 155c, and 156c, lower confining channels 160c, 161c, 162c, 163c, 164c, 165c, and 166c each of which has a predetermined diameter are formed, respectively. As the upper substrate 1, the intermediate substrate 2, and the lower substrate 3 are bound together to form a single body 100, the upper confining channels 160a, 161a, 162a, 163a, 164a, 165a, and 166a, holes 160b, 161b, 162b, 163b, 164b, 165b, and 166b, and the lower confining channels 160c, 161c, 162c, 163c, 164c, 165c, and 166c are interconnected, respectively, thereby resulting in individual hole units. The holes 160b, 161b, 162b, 163b, 164b, 165b, and 166b are independently opened or closed by microbeads that are moved by the electromagnetic force generated by corresponding upper and lower electromagnet pairs 190a and 190b, 191a and 191b, 192a and 192b, 193a and 193b, 194a and 194b, 195a and 195b, and 196a and 196b, wherein the upper and lower electromagnet pairs are disposed on the top surface of the upper substrate and the bottom surface of the lower substrate, respectively, opposite to each other with a hole therebetween. To prevent the microbeads from dropping into and plugging the holes, it is preferable that the confining grooves have a diameter that is 30-60% greater than that of the microbeads.

Figure 8:
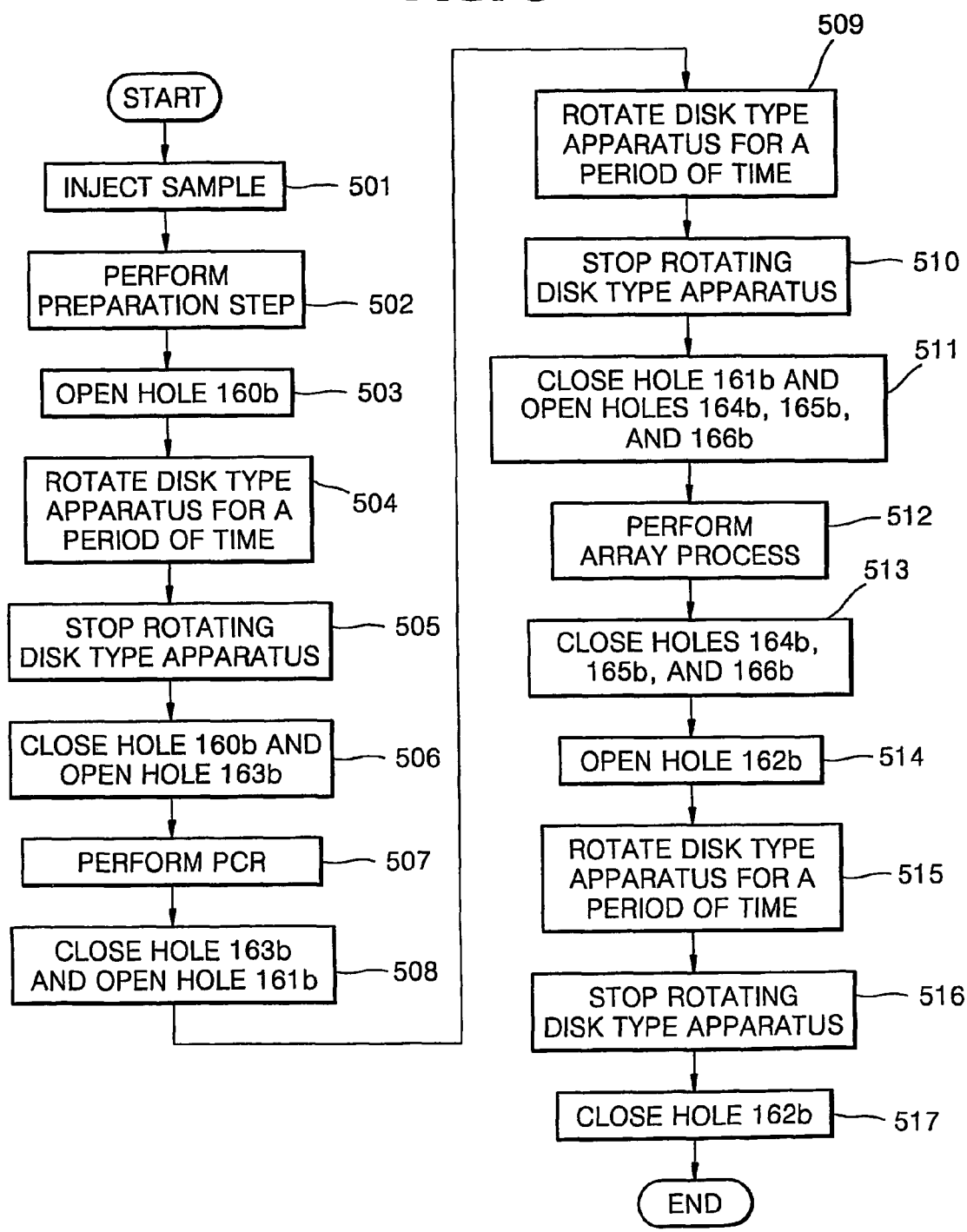
FIG. 8 is a flowchart for illustrating a method for controlling a micro valve apparatus using a microbead according to an embodiment of the present invention in a thin disk type lab-on-a-chip, such as a general CD-ROM, DVD, bio-CD, or bio-DVD.

FIG. 8 is a flowchart for illustrating a method for controlling a micro valve apparatus using a microbead according to the present invention in a lab-on-a-chip in which a thin disk type apparatus 200 is installed. The thin disk type apparatus 200 may be a general CD-ROM, DVD, bio-CD, or bio-DVD.

Opening and closing of the valves (holes) at the start and end of each of the processes (preparation, PCR, hybridization, and washing process) is controlled by on/off control of the power applied to the electromagnet pair arranged above and below each of the microbeads. Fluid flow in the apparatus is induced by the centrifugal force which occurs as the disk type apparatus 200 is rotated.

A crude blood or cellular sample is injected into the preparation chamber 130 via the sample inlet 121 (see FIG. 4) (Step 501). In the preparation step (Step 502), a DNA or RNA sample is extracted from the crude blood or cellular sample. After the preparation step, the hole 160b is opened, and the disk type apparatus is rotated for a predetermined period of time to generate a centrifugal force and stopped (Steps 503, 504, and 555), thereby transferring the extracted DNA or RNA sample into the RCR chamber 131. Next, the hole 160b is closed, and the hole 163b is opened to supply enzymes and buffer solutions required for PCR (Step 506), and the PCR is performed (Step 507). In the PCR, an additional thermal controller for thermal cycles is needed. A detailed description on the thermal controller is omitted here because the present invention directs to the micro valve apparatus. After the PCR, to carry the DNA sample to the array chamber 132, the hole 163 is closed, the hole 161b is opened, and the disk type apparatus 200 is rotated for a predetermined period of time and stopped (Steps 508, 509, and 510). Next, the hole 161b is closed, and holes 164b, 165b, and 166b are opened to supply enzymes and buffer solutions required for hybridization (Step 511), and the hybridization is performed (Step 512). The holes 164b, 165b, and 166b are closed (Step 513). Next, the hole 162b is opened, the disk type apparatus 200 is rotated for a predetermined period of time and stopped (Steps 514, 515, and 516), to collect the waste produced during the array process in the trash chamber 133. Finally, the hole 162b is closed (Step 517).

INDUSTRIAL APPLICABILITY

As described above, in the micro valve apparatus using microbeads or charged microbeads according to the present invention and the method for controlling the same, the microbeads or charged microbeads are moved upward or downward by the electromagnetic force generated by on-off control of the electromagnets or by the electric field generated by controlling the direction in which a voltage is applied to the electrode plates, so that channels are opened or closed, and the flow rate is controlled. The micro valve apparatus and the method for controlling the same according to the present invention are suitable for thin film type diagnostic assay devices, such as lab-on-a-chips, protein chips, or DNA chips, for detecting small quantities of analytes in fluids, and more suitable for interconnecting or blocking channels formed in thin disk type apparatus, including general CD-ROMs, DVDs, bio-CDs, and bio-DVDs.

What is claimed is:

1. A micro valve apparatus comprising:
an upper substrate;
an intermediate substrate;
a lower substrate;
channels as flow paths of a fluid, the channels formed between the upper and lower substrates;
a valve hole which interconnects the channels;
the valve hole formed in the intermediate substrate, wherein the valve hole includes a first diameter and a second diameter, the second diameter having a diameter greater than that of the first diameter;
wherein the second diameter includes an third diameter having a diameter greater than the microbead;
wherein a surface formed between the first diameter and the second diameter provides a contact region on the microbead for enhancing sealing of the valve hole;
chambers for storing a variety of assay buffer and for chemical reactions; the chambers formed between the upper and lower substrates;
a rotatable disk in which the channels, the chambers and the valve hole are formed; wherein the fluid in the channels flows from the center to edges of the rotatable disk by centrifugal force caused by the rotation of the rotatable disk;
upper and lower electromagnets mounted on the top and bottom of exterior surfaces of the rotatable disk, respectively, opposite to each other; and
a microbead which is moved upward or downward by the upper and lower electromagnets, to open and close the valve hole, thereby controlling fluid flow or quantity,
wherein an upper channel connecting a first chamber to the valve hole is formed recessed to a first depth in the upper substrate, and a lower channel connecting a second chamber to the valve hole is formed recessed to a second depth in the lower substrate,
wherein the first and the second chambers are interconnected with each other through the channels when the valve hole is opened,
wherein the upper substrate has a confining groove which holds the microbead and prevents it from moving away when the rotatable disk rotates.

2. A micro valve: apparatus comprising:
an upper substrate;
an intermediate substrate;
a lower substrate;
channels as flow paths of a fluid; the channels formed between the upper and lower substrates;
a valve hole which interconnects the channels; the valve hole formed in the intermediate substrate
chambers for storing a variety of assay buffer and for chemical reactions; the chambers formed between the upper and lower substrates;
a rotatable disk body in which the channels, the chambers and the valve hole are formed; wherein the fluid in the channels flows from the center to edges of the rotatable disk by centrifugal force caused by the rotation of the rotatable disk;
upper and lower electrode plates mounted on the top and bottom of exterior surfaces of the rotatable disk, respectively, opposite to each other, which generate an electric field with the application of power; and
a charged microbead which is moved upward or downward by controlling the direction in which power is applied to the upper and lower electrode plates, to open and close the valve hole, thereby controlling fluid flow and its flux or quantity,
wherein an upper channel connecting a first chamber to the valve hole is formed recessed to a first depth in the upper substrate, and a lower channel connecting a second chamber to the valve hole is formed recessed to a second depth in the lower substrate, wherein the first and the second chambers are interconnected with each other through the channels when the valve hole is opened, wherein the upper substrate has a confining groove which holds the microbead and prevents it from moving away when the rotatable disk rotates.

3. The micro valve apparatus of claim 1 or 2, wherein the body comprises a ventilating hole through which air is exhausted to allow smooth flow of the fluid.

4. The micro valve apparatus of claim 3, wherein the ventilating hole is formed in an opposite direction to the direction in which the fluid flows or a centrifugal force is exerted.

5. The micro valve apparatus of claim 1 or 2, wherein the body is formed of a material selected from the group consisting of plastic, polymethylmethacrylate (PMMA), glass, mica, and silica.

6. The micro valve apparatus of claim 1 or 2, wherein the microbead is formed of a material selected from the group consisting of ferroelectric particles, paramagnetic particles, magnetic particles, diamagnetic particles, metal particles, metal-coated plastic particles and metal-coated glass particles.

7. The micro valve apparatus of claim 1 or 2, wherein the microbead has a diameter of 1 μm-1 mm.

8. The micro valve apparatus of claim 1 or 2, wherein the valve hole is rounded corresponding to a curvature of the microbead.

9. The micro valve apparatus of claim 1, wherein the valve hole includes an fourth diameter having a diameter smaller than the microbead.

10. The micro valve apparatus of claim 1, wherein each of the upper and lower electromagnets is a thin electromagnet with an air core.

11. A method for controlling the micro valve apparatus of claim 1, the method comprising:
    in order to block the channels by closing the hole of the micro valve apparatus, cutting off the power applied to the upper electromagnet and applying power to the lower electromagnet to attract the microbead to the hole; and
    in order to interconnect the channels with each other by opening the hole, cutting off the power applied to the lower electromagnet and applying power to the upper electromagnet to attract the microbead so as to be removed from the hole.

12. A method for controlling the micro valve apparatus of claim 2, the method comprising:
    in order to block the channels by closing the hole of the micro valve apparatus, applying a voltage of the same polarity as the charge of the microbead to the upper electrode plate to repel the charged microbead and applying a voltage of the opposite polarity to the lower electrode plate to attract the charged microbead to the hole; and
    in order to interconnect the channels with each other by opening the hole, applying a voltage of the same polarity as the charge of the microbead to the lower electrode plate to repel the charged microbead and applying a voltage of the opposite polarity to the upper electrode plate to attract the charged microbead so as to be removed from the hole.

13. A nucleic acid assay device in which fluid flow between chambers is controlled by a micro valve apparatus of claim 1 or 2, the device comprising:
    a sample injection unit via which a nucleic acid containing sample is injected;
    a preparation chamber where DNAs or RNAs are prepared from the nucleic acid containing sample;
    a PCR (polymerase chain reaction) chamber where the DNAs or RNAs are amplified through PCR or RT-PCR;
    an array chamber where the amplified DNAs or cDNAs are hybridized to a capture probe;
    a trash chamber where the non-hybridized waste from the array chamber is collected; and
    a plurality of chambers for storing a variety of enzymes and buffer solutions required for processes.

14. The nucleic acid assay device of claim 13, being constructed as a lab-on-a-chip where the preparation chamber, the PCR chamber, the trash chamber, channels, and holes are formed in a thin disk type body.

15. The nucleic acid assay device of claim 14, wherein
    opening or closing of the valve holes of the micro valve apparatus at the start and end of each of the processes is controlled by the upper and lower electromagnets or by controlling the direction in which power is applied to the upper and lower electrode plates, and the fluid flow is induced by the centrifugal force which occurs as the disk type body is rotated.

16. A nucleic acid assay method in the nucleic acid assay device of claim 15, the method comprising:
    (a) injecting a nucleic acid containing sample into the preparation chamber via the sample injection unit;
    (b) preparing DNAs or RNAs from the nucleic acid containing sample;
    (c) opening a first hole between the preparation chamber and the PCR chamber and rotating the nucleic acid assay device for a predetermined period of time, to transfer the prepared DNAs or RNAs to the PCR chamber;
    (d) closing the first hole, opening a second hole between a chamber which store enzymes and buffer solutions required for PCR and the POR chamber, and performing the PCR or RT-PCR to amplify the DNAs or RNAs;
    (e) after the PCR or RT-PCR has completed, closing the second hole, opening a third hole between the PCR chamber and the array chamber, and rotating the nucleic acid assay device for a predetermined period of time, to transfer the amplified DNAs or cDNAs to the array chamber;
    (f) closing the third hole, opening a fourth hole between a chamber which stores enzymes and buffer solutions required for hybridization and the array chamber, and performing the hybridization; and
    (g) after the hybridization has completed, closing the fourth hole, opening a fifth hole between the array chamber and the trash chamber, and rotating the nucleic acid assay device for a predetermined period of time, to collect the waste from the array process within the trash chamber.

17. A thin film type assay device in which fluid flow between chambers is controlled by a micro valve apparatus of claim 1 or 2, the device comprising:
    a sample injection unit via which a sample is injected;
    a preparation chamber;
    an array chamber having capture probes;
    a trash chamber where the waste from the array chamber is collected; and
    a plurality of chambers for storing a variety of enzymes or buffer solutions required for processes.

18. A micro valve apparatus comprising:
    an upper substrate;
    an intermediate substrate;
    a lower substrate;

channels as flow paths of a fluid; the channels formed between the upper and lower substrates;

a valve hole which interconnects the channels, the valve hole formed in the intermediate substrate;

chambers for storing a variety of assay buffer and for chemical reactions; the chambers formed between the upper and lower substrates;

an array chamber having capture probes for detecting a small quantity of an analyte in a fluid;

upper and lower electromagnets mounted on the top and bottom of exterior surfaces of the rotatable disk;

a rotatable disk in which the channels, the chambers, the array chamber and the valve hole are formed; wherein the fluid in the channels flows from the center to edges of the rotatable disk by centrifugal force caused by the rotation of the rotatable disk; and a microbead which is moved upward or downward by magnetic force generated by the upper and lower electromagnets, to open and close the valve hole, thereby controlling fluid flow and or quantity, wherein an upper channel connecting a first chamber to the valve hole is formed recessed to a first depth in the upper substrate, and a lower channel connecting a second chamber to the valve hole is formed recessed to a second depth in the lower substrate, wherein the first and the second chambers are interconnected with each other through the channels when the valve hole is opened, wherein the upper substrate has a confining groove which holds the microbead and prevents it from moving away when the rotatable disk rotates.

19. An apparatus, comprising:

a rotatable disk having a rotation axis and having channels carrying fluid via centrifugal force toward an outer edge of the disk, comprising:

a first substrate having a first fluid chamber and a first substrate outside surface;

a second substrate having a second fluid chamber and a second substrate outside surface;

a third substrate in between the first and second substrates;

a first electromagnet formed on the first substrate outside surface;

a second electromagnet formed on the second substrate outside surface;

a valve formed in the third substrate connecting the first and second chambers in a direction parallel to the axis and perpendicular to the force via an opening;

a groove formed in the third substrate in alignment with the opening; and a cylindrical microbead positioned in the valve and closing the opening by moving parallel to the axis responsive to the electromagnets and being held in alignment with the opening by the groove.

* * * * *